United States Patent [19]

Uno et al.

[11] Patent Number: 5,756,784

[45] Date of Patent: May 26, 1998

[54] AMIDES, METHOD FOR PREPARING THE AMIDES, AND DETERGENT COMPOSITIONS CONTAINING THE AMIDES

[75] Inventors: Mitsuru Uno; Tetsuya Miyajima; Tomohito Kitsuki; Katsumi Kita, all of Wakayama, Japan

[73] Assignee: Kao Corporation, Tokyo, Japan

[21] Appl. No.: 646,767

[22] Filed: May 8, 1996

[30] Foreign Application Priority Data

| | | | |
|---|---|---|---|
| May 9, 1995 | [JP] | Japan | 7-110335 |
| May 17, 1995 | [JP] | Japan | 7-118219 |
| Jun. 5, 1995 | [JP] | Japan | 7-137735 |
| Jun. 5, 1995 | [JP] | Japan | 7-137736 |

[51] Int. Cl.$^6$ ............................................. C07C 233/05
[52] U.S. Cl. .................. 554/52; 554/51; 558/25; 558/47; 560/169; 560/170; 564/159
[58] Field of Search ........................ 564/159; 560/170, 560/169; 562/103; 510/490, 499, 503, 501, 502, 494, 126; 554/51, 52; 558/25, 47

[56] References Cited

U.S. PATENT DOCUMENTS

| | | | |
|---|---|---|---|
| 3,689,544 | 9/1972 | Scanlon et al. | 260/534 E |
| 4,851,138 | 7/1989 | Jaroschek et al. | 252/88 |
| 5,318,727 | 6/1994 | Ohtawa et al. | 252/547 |

FOREIGN PATENT DOCUMENTS

| | | |
|---|---|---|
| 0 463 801 | 1/1992 | European Pat. Off. . |
| 463801 | 1/1992 | European Pat. Off. . |
| 1 383 741 | 2/1975 | United Kingdom . |

*Primary Examiner*—Shailendra Kumar
*Attorney, Agent, or Firm*—Oblon, Spivak, McClelland, Maier & Neustadt, P.C.

[57] ABSTRACT

An amide represented by the following formula (1):

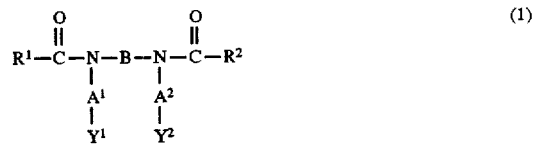

wherein $R^1$ and $R^2$ are C1–C24 alkyl, etc.; B is C2–C10 alkylene, etc.; $A^1$ and $A^2$ are C1–C6 alkylene, etc.; $Y^1$ and $Y^2$ are

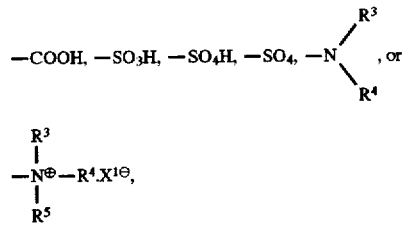

wherein $R^3$, $R^4$, and $R^5$ are C1–C4 alkyl, etc., and $X^1$ is halogen; or a salt of the amide and detergent compositions containing the amide or salt are mild to the skin or hair, provide a pleasant sensation to the skin or hair, and have excellent latherability and emulsion stability. These compounds are useful as components of various detergents and cosmetic compositions, emulsifiers, and conditioners.

12 Claims, No Drawings

AMIDES, METHOD FOR PREPARING THE AMIDES, AND DETERGENT COMPOSITIONS CONTAINING THE AMIDES

BACKGROUND OF THE INVENTION

1. Field of the Invention

The present invention relates to novel amides useful as components of detergents for the skin and hair, as emulsifiers in cosmetic compositions, or as conditioning agents. The invention also relates to methods for preparing the amides as well as detergent compositions containing the amides.

2. Description of the Related Art

Conventionally, surfactants such as alkyl sulfates, polyoxyethylene alkyl sulfates, and alkylbenzene sulfonates have been used as detergents and emulsifiers. However, most of them have the problem that they give relatively strong stimulation to the skin during use. Therefore, certain surfactants which are mild to the skin, e.g., alkyl phosphates and acylated amino acids, have come to be used as bases or emulsifiers incorporated in hair care or skin cosmetic compositions or as detergents for the skin, etc.

As consumer demand has become diversified and quality-oriented, improved properties are required for these products, including not only mildness to the skin but also good latherability and a pleasant sensation to the skin. The surfactants mentioned above do not necessarily satisfy such needs.

A variety of quaternary ammonium salts, which are categorized as cationic surfactants, are used as conditioners for the hair and finishing compounds. Quaternary ammonium salts, however, have proven useful only within very limited fields because they have insufficient latherability and are not necessarily mild to the skin. Thus, they are not used as bases or emulsifiers in hair-care or skin cosmetic compositions, nor as detergents for the skin, etc.

The present inventors found that 2-hydroxypropanediamine derivatives have excellent latherability and are mild to the skin, and they previously filed a pertinent patent application (WP95/01955). Nevertheless, compounds having better properties are still desired.

Under the above circumstances, the present inventors conducted extensive studies and found that the new amides represented by formula (1) described hereinbelow provide a pleasant sensation to the skin without giving irritation to the skin and have excellent latherability and emulsion stability. The present invention was accomplished based on this finding.

SUMMARY OF THE INVENTION

Accordingly, an object of the present invention is to solve the above-mentioned problems and to provide compounds which are mild to the skin, have excellent latherability, provide a pleasant sensation to the skin, and are useful as bases of hair and skin cosmetic compositions, detergents, emulsifiers, conditioners, etc.

In one aspect of the present invention, there is provided an amide represented by the following formula (1):

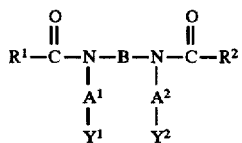
(1)

wherein
$R^1$ and $R^2$ are identical to or different from each other, each independently representing linear or branched C1–C24 alkyl or alkenyl which may be substituted by hydroxyl;
B represents linear or branched C2–C10 alkylene which may be substituted by hydroxyl or B represents a group
—$CH_2CH(OH)CH_2O(CH_2CH_2O)_pCH_2CH(OH)CH_2$—
wherein p is an integer from 0 to 2 inclusive;
$A^1$ and $A^2$ are identical to or different from each other, each independently representing linear or branched C1–C6 alkylene which may be substituted by hydroxyl or carboxyl; and
$Y^1$ and $Y^2$ are identical to or different from each other, each independently representing —COOH, —$SO_3H$, —$SO_4H$,

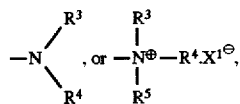

wherein $R^3$, $R^4$, and $R^5$ are identical to or different from one another and each independently represents linear or branched C1–C4 alkyl or alkenyl which may be substituted by hydroxyl and $X^1$ represents a halogen atom. There is also provided a salt of the amide as well as a method for preparing the amide and the salt.

The present invention also provides a detergent composition containing the amide represented by formula (1) or a salt thereof.

DETAILED DESCRIPTION OF THE INVENTION AND PREFERRED EMBODIMENTS

In formula (1), illustrative linear or branched C1–C24 alkyl or alkenyl groups which are represented by $R^1$ or $R^2$ include the following.

Examples of linear alkyl groups include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, heneicosyl, docosyl, tricosyl, and tetracosyl. Examples of branched alkyl groups include, for example, methyl hexyl, ethyl hexyl, methyl heptyl, ethyl heptyl, methyl nonyl, methyl undecyl, methyl heptadecyl, hexyldecyl, and octyldecyl.

Examples of linear alkenyl groups include ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, heneicosenyl, docosenyl, tricosenyl, and tetracosenyl. Examples of branched alkenyl groups include methylhexenyl, ethylhexenyl, methylheptenyl, ethylheptenyl, methylnonenyl, methylundecenyl, methylheptadecenyl, hexyldecenyl, and octyldecenyl.

Regarding linear or branched alkyl groups substituted by a hydroxyl group, the position of hydroxyl substitution is not particularly limited. Examples of the hydroxy-substituted linear or branched alkyl groups include hydroxymethyl, hydroxyethyl, hydroxypropyl, hydroxybutyl, hydroxypentyl, hydroxyhexyl, hydroxyheptyl, hydroxyoctyl, hydroxynonyl, hydroxydecyl, hydroxyundecyl, hydroxydodecyl, hydroxytridecyl, hydroxytetradecyl, hydroxypentadecyl, hydroxyhexadecyl, hydroxyheptadecyl, hydroxyoctadecyl, hydroxynonadecyl, hydroxyicosyl, hydroxyheneicosyl, hydroxydocosyl, hydroxytricosyl, hydroxytetracosyl, hydroxymethylhexyl, hydroxyethylhexyl, hydroxymethylheptyl, hydroxyethylheptyl, hydroxymethylnonyl, hydroxymethylundecyl, hydroxymethylheptadecyl, hydroxyhexyldecyl, and hydroxyoctyldecyl.

Regarding linear or branched alkenyl groups substituted by a hydroxyl group, the position of hydroxyl substitution is not particularly limited. Illustrative examples include hydroxyethenyl, hydroxypropenyl, hydroxybutenyl, hydroxypentenyl, hydroxyhexenyl, hydroxyheptenyl, hydroxyoctenyl, hydroxynonenyl, hydroxydecenyl, hydroxyundecenyl, hydroxydodecenyl, hydroxytridecenyl, hydroxytetradecenyl, hydroxypentadecenyl, hydroxyhexadecenyl, hydroxyheptadecenyl, hydroxyoctadecenyl, hydroxynonadecenyl, hydroxyicosenyl, hydroxyheneicosenyl, hydroxydocosenyl, hydroxytricosenyl, hydroxytetracosenyl, hydroxymethylhexenyl, hydroxyethylhexenyl, hydroxymethylheptenyl, hydroxyethylheptenyl, hydroxymethylnonenyl, hydroxymethylundecenyl, hydroxymethylheptadecenyl, hydroxyhexyldecenyl, and hydroxyoctyldecenyl.

Of the listed species of $R^1$ and $R^2$, preferred ones are linear or branched C1–C18 alkyl or alkenyl which may be substituted by hydroxyl, with linear or branched C7–C15 alkyl which may be substituted by hydroxyl being more preferred and C7–C15 linear alkyl being particularly preferred considering properties including latherability and detergency. Although the two $R^1$s in one molecule may be identical or different from each other, they are preferably be identical.

In formula (1), illustrative linear or branched C2–C10 alkylene groups which may be substituted by hydroxyl and represented by B include ethylene, trimethylene, propylene, tetramethylene, pentamethylene, hexamethylene, heptamethylene, octamethylene, nonamethylene, decamethylene, and 2-hydroxytrimethylene. Of the listed species, linear C2–C10 alkylene which may be substituted by hydroxyl is preferred, with linear C2–C6 alkylene which may be substituted by hydroxyl being more preferred and linear C2–C6 alkylene being particularly preferred.

The number p in —$CH_2CH(OH)CH_2O(CH_2CH_2O)_p$ $CH_2CH(OH)CH_2$— represented by B is an integer ranging from 0 to 2. The number 0 is particularly preferred.

In formula (1), illustrative linear or branched C1–C6 alkylene groups which may be substituted by hydroxyl or carboxyl and represented by $A^1$ or $A^2$ include methylene, ethylene, trimethylene, propylene, tetramethylene, pentamethylene, hexamethylene, 2-hydroxytrimethylene, 1-carboxyethylene, and 2-carboxyethylene. Of the listed species, C1–C4 alkylene which may be substituted by hydroxyl or carboxyl are preferred. Linear C1–C6 alkylene groups which do not have any substituent as well as linear C2–C4 alkylene groups which do not have any substituent are also preferred.

In formula (1), among the listed groups for $Y^1$ or $Y^2$ in other words, among —COOH, —$SO_3H$, —$SO_4H$,

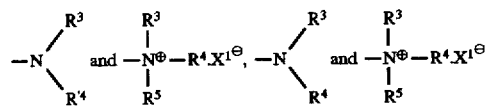

are more preferred, and

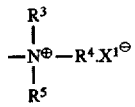

is particularly preferred.

As examples of linear or branched C1–C4 alkyl or alkenyl which may be substituted by hydroxyl, and represented by $R^3$, $R^4$, or $R^5$, those groups listed for $R^1$ having 1 to 4 carbon atoms are mentioned. Of such groups, methyl and ethyl are preferred, and methyl is particularly preferred. $R^3$, $R^4$, and $R^5$ which are concurrently present in one molecule in a total number of 6 may be identical or different from one another. Preferably, they are identical. Preferable halogen atoms represented by $X^1$ include fluorine, chlorine, bromine, and iodine. Particularly, chlorine and bromine are preferred with chlorine being most preferred.

Preferred compounds in the present invention are those represented by formula (1) in which $R^1$ and $R^2$ are identical or different from each other, and each of $R^1$ and $R^2$ independently represents linear or branched C1–C18 alkyl or alkenyl; B is linear or branched C2–C10 alkylene which may be substituted by hydroxy; $A^1$ and $A^2$ are linear C1–C6 alkylene; and $Y^1$ and $Y^2$ are

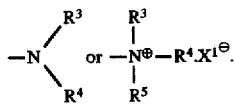

When the compounds (1) of the present invention have a carboxyl group (—COOH), a sulfo group (—$SO_3H$), or a sulfate group (—$SO_4H$), they are able to form salts with a variety of basic substances. Examples of such salts include alkali metal salts, alkaline earth metal salts, amine salts, basic amino acid salts, and ammonium salts. More specifically, salts having counterions such as sodium, potassium, lithium, magnesium, calcium, trimethylamine, triethylamine, tributylamine, monoethanolamine, diethanolamine, triethanolamine, lysine, arginine, chlorine, or ammonia are useful. Particularly, sodium salts, potassium salts, and ammonium salts are preferred.

The amides of the present invention may be prepared, for example, by the following reaction scheme:

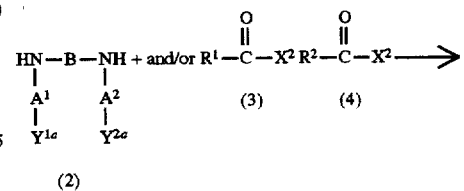

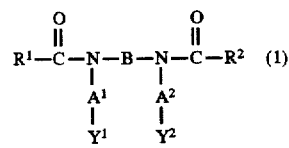

wherein $Y^{1a}$ and $Y^{2a}$ are identical or different from each other, each independently representing —COOH, —$SO_3H$, —$Sl_4H$, alkoxycarbonyl, nitrile, hydroxyl, or

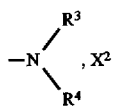

represents hydroxyl, halogen, or alkoxyl, and $R^1$, $R^2$, B, $A^1$, $A^2$, $R^3$, and $R^4$ have the same meanings as defined above.

In more detail, an amine compound (2) and acyl compounds (3) and/or (4) are first reacted. If $Y^{1a}$ or $Y^{2a}$ is alkoxycarboxyl or nitrile, hydrolysis is preferably performed in the presence of a basic catalyst, whereas if $Y^{1a}$ or $Y^{2a}$ are hydroxyl, a sulfating agent is preferably reacted. If $Y^{1a}$ or $Y^{2a}$ is

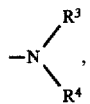

a halide represented by $R^5X^1$ (wherein $R^5$ denotes linear or branched C1–C4 alkyl or alkenyl which may be substituted by hydroxyl and $X^1$ denotes a halogen atom) is reacted as desired, thereby obtaining an amide compound (1). Reaction conditions of the amine compound (2) and acyl compound (3) vary depending on the species of $Y^{1a}$ and $Y^{2a}$ in the amine compound (2). When $Y^{1a}$ and $Y^{2a}$ are

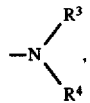

the following method A may be performed, whereas when $Y^{1a}$ and $Y^{2a}$ are —COOH, —SO$_3$H, —SO4H, alkoxycarbonyl, nitrile, or hydroxyl, the following method B may be performed.

Method A:

If $X^2$ in compound (3) and/or compound (4) is a halogen atom, compound (2) may be reacted with compound(s) (3) and/or (4) in the presence of an inert solvent in a temperature range between 0° and about 100° C., preferably between 0° and 40° C. The amount of compound(s) (3) and/or (4) is preferably about 1 to 2 equivalents with respect to the two secondary amino groups of compound (2). In this case, by adding a variety of alkali agents, hydrogen halide produced from the reaction can be neutralized, making the reaction proceed more smoothly. Examples of alkali agents include alkali metal hydroxides, alkali metal carbonates, and trisubstituted amines. Particularly preferred alkali agents are sodium hydroxide, potassium hydroxide, sodium carbonate, potassium carbonate, sodium hydrogencarbonate, potassium hydrogencarbonate, trimethylamine, and triethylamine. Inert solvents which may be used in this reaction are water, ethers, aliphatic hydrocarbons, etc. These solvents may be used singly or in combination of two or more.

If $X^2$ in compound (3) and/or compound (4) is hydroxyl or alkoxyl, compound (2) may be reacted with compounds (3) and/or (4) in the presence or absence of an inert solvent in the temperature range between about 50° and 200° C. The amount of compounds (3) and/or (4) is preferably about 1 to 10 equivalents with respect to the two secondary amino groups of compound (2). In this case, if a variety of acid or base catalysts coexist, the reaction proceeds more smoothly. Examples of preferred acid catalysts or base catalysts include p-toluenesulfonic acid, boron trifluoride, aluminum trichloride, sodium hydroxide, potassium hydroxide, sodium carbonate, potassium carbonate, sodium hydrogencarbonate, and potassium hydrogencarbonate. Inert solvents which may be used in this reaction are ethers, aliphatic hydrocarbons, aromatic hydrocarbons, etc. These solvents may be used singly or in combination of two or more.

In this reaction, if $R^1$ and $R^2$ of compounds (3) and (4) are differently selected, compounds (1) in which $R^1$ and $R^2$ differ from each other can be prepared. However, in view of simplicity, it is preferred to use a single compound (3) and to prepare a compound (1) in which $R^1$ and $R^2$ are identical to each other. In the case in which compound (1) obtained in this reaction is a free amine, the compound (1) may be neutralized with a hydrogen halide such as hydrogen fluoride or hydrogen chloride, if needed, and thus may be converted into a salt. Alternatively, in the case in which compound (1) is obtained in the form of a salt through a reaction with a byproduct hydrogen halide, the compound may be neutralized using a suitable base if necessary and thus may be converted into a free amine.

In the thus-obtained compound, $Y^{1a}$ and $Y^{2a}$ are

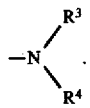

If this compound is reacted with $R^5$–$X^1$ as needed, a compound in which $Y^{1a}$ and $Y^{2a}$ are

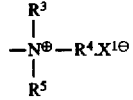

can be obtained.

The reaction between this compound and $R^5$–$X^1$ may be performed in the presence of an inert solvent in the temperature range between about 20° and 150° C., preferably between 60° and 120° C. The amount of $R^5$–$X^1$ is preferably about 2 to 10 equivalents with respect to the two amino groups of this compound. In this case, by adding a variety of alkali agents, hydrogen halide produced from the decomposing reaction of $R^5$–$X^1$ can be neutralized, enabling the reaction to proceed more smoothly. Examples of alkali agents include alkali metal hydroxides and alkali metal carbonates. Particularly preferred alkali agents are sodium hydroxide, potassium hydroxide, sodium carbonate, potassium carbonate, sodium hydrogencarbonate, and potassium hydrogencarbonate. Inert solvents which may be used in this reaction are water, alcohol, aliphatic hydrocarbons, aromatic hydrocarbons, etc. These solvents may be used singly or in combination of two or more. In particular, water, lower alcohols, or mixtures of water and lower alcohols are preferred.

In this reaction, if $R^5$ of $R^5$–$X^1$ is selected to be different from $R^3$ and $R^4$ in compound (1), or if two or more compounds having $R^5$s identical to or different from $R^3$ and $R^4$ in compound (1) are used in combination, compounds (1) having two or more species of $R^5$ can be prepared. However, in view of simplicity, it is preferred to use a compound $R^5$–$X^1$ in which $R^5$ is identical to $R^3$ and $R^4$ of compound (1) to prepare a compound (1) in which $R^3$, $R^4$, and $R^5$ are identical to one another.

Method B:

The amine compound (2) used in Method B may be prepared using a known method, for example, by reacting a diamine with a halide, an olefin compound, an epoxy compound, or sultones.

Specific examples of diamines include ethylenediamine, trimethylenediamine, propylenediamine, and hexamethylenediamine, 2-hydroxytrimethylenediamine. Specific examples of halides includes sodium chloroacetate, sodium bromoacetate, sodium chloropropionate, sodium bromopropionate, sodium 3-chloro-2-hydroxypropanesulfonate, 2-chloroethanol, and 3-chloropropanol. Specific examples of olefin compounds include methyl acrylate, ethyl acrylate, propyl acrylate, acrylonitrile, methyl maleate, ethyl maleate, propyl maleate, methyl fumarate, ethyl fumarate, and propyl fumarate. Specific examples of sultones include propanesultone and butanesultone.

In cases where amine compound (2) dissolves only in water amine compound (2) may be reacted with compound (s) (3) and/or (4) (acyl halide) in which $X^2$ is halogen in the presence of an aqueous inert solvent in the temperature range between about 0° and 50° C., preferably between 10° and 30° C. The amount of acyl halide is preferably about 2 to 5 times by moles as much as the amine compound (2). Examples of preferred aqueous inert solvents include water, water/acetone, and water/methylethylketone. Solvent mixtures of water and acetone are particularly preferred.

In cases where amine compound (2) dissolves only in organic solvents other than water, amine compound (2) may be reacted with acyl halide in the absence of solvent or in the presence of an inert solvent in the temperature range between about 0° and 50° C., preferably between 0° and 30° C. The amount of acyl halide is preferably about 2 to 5 times by moles as much as the amine compound (2). Reaction of amine compound (2) and acyl compound(s) (3) and/or (4) (carboxylic acid or carboxylic esters) in which $X^2$ is halogen is carried out in the absence of solvent or in the presence of an inert solvent in the temperature range between about 50° and 200° C., and preferably between 80° and 160° C. Examples of inert solvents include toluene and xylene. If acyl compounds (3) and (4) are carboxylates, addition of a basic catalyst such as alkoxide to the reaction system may reduce the reaction temperature.

When an amine compound (2) in which $Y^{1a}=Y^1$ and $Y^{2a}=Y^2$ is used, compound (1) of the present invention is directly obtained from the above reaction. If $Y^{1a}$ and $Y^{2a}$ in the amine compound (2) is alkoxycarbonyl or nitrile, $Y^{1a}$ and $Y^{2a}$ may be converted into a carboxyl group by hydrolysis in the presence of a basic catalyst after the above reaction, or, if $Y^{1a}$ and $Y^{2a}$ in the amine compound (2) is hydroxyl, $Y^{1a}$ and $Y^{2a}$ may be converted into a sulfate group by further reaction with a sulfating agent such as chlorosulfonic acid or $SO_3$ gas after the above reaction, to obtain compound (1) of the present invention.

The thus-obtained compounds (1) of the present invention can be converted into salts by neutralizing using a basic substance if necessary. Examples of basic substances include sodium hydroxide, potassium hydroxide, lithium hydroxide, magnesium hydroxide, calcium hydroxide, ammonia, trimethylamine, triethylamine, tributylamine, alkanolamine (monoethanolamine, diethanolamine, triethanolamine, etc.), lysine, arginine, and choline. Of these, alkali metal hydroxides such as sodium hydroxide and potassium hydroxide are particularly preferred.

When the reaction of method A or method B is completed, the reaction mixture may contain inorganic salts, unreacted amine compounds (2), ester derivatives, or fatty acids in addition to amides (1) of the present invention. In the present invention, although reaction products may be used as they are, they may be used after a known purification process such as solvent separation, ion exchange chromatography, recrystallization, and electrophoresis.

The amides (1) of the present invention are mild to the skin, give a pleasant sensation to the skin, and have excellent detergency and latherability. In view of these advantages, the amides of the invention are useful as a variety of detergents for the skin, hair, tableware, and for clothes. Moreover, since the amides (1) of the invention have stable emulsifying properties, the amides (1) of the invention are useful as emulsifiers for formulating skin and hair cosmetic compositions as well as conditioning agents. Particularly, amides (1) are advantageously used as detergents. The amount of compounds (1) to be incorporated in a detergent base is not particularly limited. It is generally 0.1–80% by weight, preferably 1–50% by weight, depending on use, etc. relative to the total weight of the detergent composition.

When compounds (1) of the present invention are used for the above purposes, known additives may be incorporated including a variety of surfactants, humectants, bactericides, emulsifiers, thickeners, pearl-hue imparting agents, divalent metal ion scavengers, alkali agents, inorganic salts, antiredeposition agents, enzymes, effective chlorine scavengers, reducing agents, bleaching agents, fluorescent dyes, solubilizers, perfumes, anticaking agents, activators for enzymes, antioxidants, preservatives, colorants, blueing agents, bleach-activators, enzyme stabilizers, phase regulators, and penetrants.

EXAMPLES

The present invention will next be described by way of examples, which should not be construed as limiting the invention thereto.

Example 1

2,14-Dimethyl-2,6,10,14-tetrazapentadecane (16.3 g, 0.067 mol) synthesized using a known method, triethylamine (13 g, 0.13 mol), and methylene chloride (200 ml) were placed in a 500 ml four-necked round flask, and the mixture was cooled on ice. Dodecanoylchloride (29 g, 0.13 mol) was added dropwise over 1 hour to the flask while the contents of the flask were stirred under nitrogen. The mixture was stirred for 24 more hours at room temperature. The solid which precipitated was removed by filtration, after which water was added for washing. Methylene chloride was removed from the organic phase under reduced pressure. The residue was purified by column chromatography (packed with Kieselgel 60, product of Merck; eluent:chloroform/methanol=7:1 (v/v)) to obtain 11.7 g of 4,8-bis(1-oxododecyl)-1,1-di(dimethylamino)-4,8-diazaundecane. Yield: 30 wt %.

The thus-obtained compound (10 g, 0.017 mol), methyl chloride (2.1 g, 0.04 mol), sodium carbonate (0.36 g, 0.0034 mol), isopropyl alcohol (100 ml), and water (20 ml) were placed into a 500-ml autoclave, and the temperature was elevated to 70° C. This temperature (70° C.) was maintained for 6 hours, and the flask was then allowed to cool to room temperature. The solvent was evaporated under reduced pressure. The residue was dissolved in chloroform (300 ml) and washed with water. Chloroform was distilled off under reduced pressure to give 11 g of 4,8-bis(1-oxododecyl)-1,11-di(trimethylammonium)-4,8-diazaundecane dichloride. Yield: 95 wt %. High performance liquid chromatography (column: RP-18 (Merck), eluent:methanol/water=9:1 (v/v), 20 mM tetrabutylammonium bromide) confirmed that this compound was not a mixture but a single product.

$^1$H-NMR(CD$_3$OD-CDCl$_3$):δ (ppm)
0.88 (6H, triplet, a)
1.27 (32H, singlet, b)

1.62 (4H, broad singlet, c)
1.95–2.25 (6H, complex multiplet, d)
2.25–2.7 (4H, complex multiplet, e)
3.17 (6H, singlet, f-1)
3.18 (6H, singlet, f-2)
3.22 (6H, singlet, f-3)
3.25–3.75 (12H, complex multiplet, g)

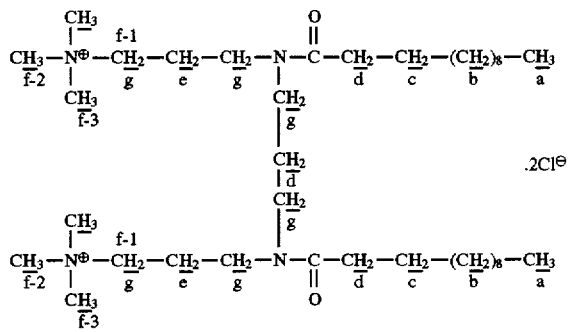

Example 2

2,17-Dimethyl-2,6,13,17-tetrazaoctadecane (30 g, 0.10 mol) synthesized using a known method, triethylamine (20 g, 0.20 mol), and methylene chloride (600 ml) were placed in a 1-liter four-necked round flask, and the mixture was cooled on ice. Hexadecanoylchloride (55 g, 0.20 mol) was added dropwise over 3 hours to the flask while the contents of the flask were stirred under nitrogen. The mixture was stirred for 24 more hours at room temperature. The solid which precipitated was removed by filtration, and the solvent was removed under reduced pressure. The residue was purified by column chromatography (packed with Kieselgel 60 (product of Merck), eluent:chloroform/methanol=7:1 (v/v)) to obtain 11 g of 4,11-bis(1-oxohexadecyl)-1,14-di(dimethylamino)-4,11-diazaundecane. Yield: 15 wt %.

The thus-obtained compound (10 g, 0.013 mol), methyl chloride (1.6 g, 0.031 mol), sodium carbonate (0.28 g, 0.0026 mol), isopropyl alcohol (100 ml), and water (20 ml) were placed into a 500-ml autoclave, and the temperature was elevated to 70° C. This temperature (70° C.) was maintained for 6 hours, and the flask was then allowed to cool to room temperature. The solvent was evaporated under reduced pressure. The residue was dissolved in chloroform (300 ml) and washed with water. Chloroform was distilled off under reduced pressure to give 10 g of 4,11-bis(1-oxohexadecyl)-1,14-di(trimethylammonium)-4,11-diazaundecane dichloride. Yield: 95 wt %. High performance liquid chromatography (column: RP-18 (Merck), eluent:methanol/water=9:1 (v/v) (20 mM tetrabutylammonium bromide)) confirmed that this compound was not a mixture but a single product.

$^1$H-NMR(CD$_3$OD-CDCl$_3$):δ (ppm)
0.88 (6H, triplet, a)
1.27 (52H, singlet, b)
1.70 (8H, broad singlet, c)
1.95–2.25 (4H, complex multiplet, d)
2.25–2.70 (4H, complex multiplet, e)
3.17 (6H, singlet, f-1)
3.18 (6H, singlet, f-2)

3.22 (6H, singlet, f-3)
3.25–3.75 (12H, complex multiplet, g)

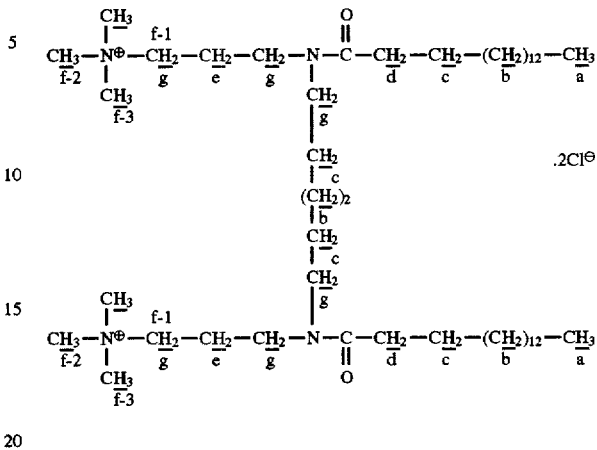

Example 3

2,14-Dimethyl-8-hydroxy-2,6,10,14-tetrazapentadecane (17 g, 0.067 mol) synthesized in accordance with the method described in DE2616411, triethylamine (13 g, 0.13 mol), and methylene chloride (200 ml) were placed in a 500-ml four-necked round flask, and the mixture was cooled on ice. Dodecanoylchloride (29 g, 0.13 mol) was added dropwise over 1 hour to the flask while the contents of the flask were stirred under nitrogen. The mixture was stirred for 24 more hours at room temperature. The solid which precipitated was removed by filtration, after which water was added for washing. Methylene chloride was removed from the organic phase under reduced pressure. The residue was purified by column chromatography (packed with Kieselgel 60 (product of Merck), eluent:chloroform/methanol=7:1 (v/v)) to obtain 12.3 g of 4,8-bis(1-oxododecyl)-1,11-di(dimethylamino)-4,8-diazaundecane. Yield: 30 wt %.

The thus-obtained compound (12 g, 0.02 mol), methyl chloride (20 g, 0.36 mol), sodium carbonate (0.4 g, 0.004 mol), isopropyl alcohol (100 ml), and water (20 ml) were placed into a 500-ml autoclave, and the temperature was elevated to 70° C. This temperature (70° C.) was maintained for 6 hours, and the flask was then allowed to cool to room temperature. The solvent was evaporated under reduced pressure. The residue was dissolved in chloroform (300 ml) and washed with water. Chloroform was distilled off under reduced pressure to give 13.6 g of 4,8-bis(1-oxododecyl)-1,11-di(trimethylammonium)-6-hydroxy-4,8-diazaundecane chloride. Yield: 95 wt %. High performance liquid chromatography (column: RP-18 (Merck), eluent:methanol/water=9:1 (v/v) (20 mM tetrabutylammonium bromide)) confirmed that this compound was not a mixture but a single product.

$^1$H-NMR(CD$_3$OD-CDCl$_3$):δ (ppm)
0.88 (6H, triplet, a)
1.27 (32H, singlet, b)
1.62 (4H, broad singlet, c)
1.95–2.25 (4H, complex multiplet, d)
2.25–2.7 (4H, complex multiplet, e)
3.17 (6H, singlet, f-1)
3.18 (6H, singlet, f-2)
3.22 (6H, singlet, f-3)

3.25–3.75 (12H, complex multiplet, g)
4.06 (1H, broad singlet, h)

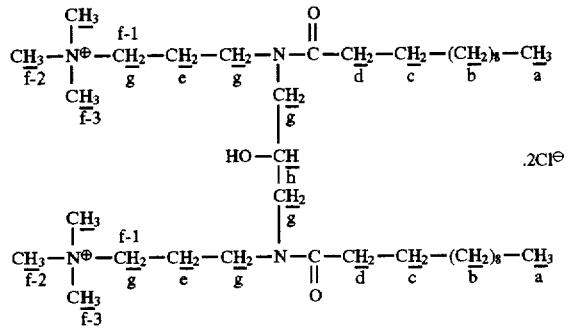

3.25–3.75 (12H, complex multiplet, g)
4.06 (1H, broad singlet, h)

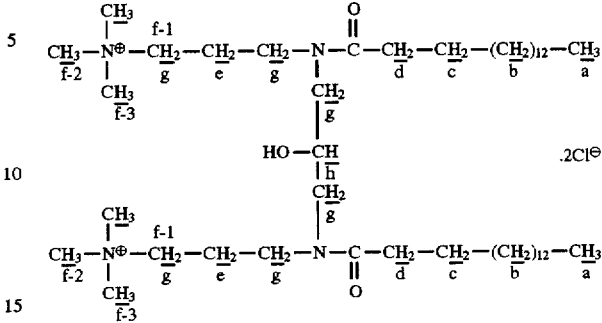

Example 4

2,14-Dimethyl-8-hydroxy-2,6,10,14-tetrazapentadecane•2HCl (30 g, 0.09 mol) synthesized in accordance with the method described in DE2616411, triethylamine (62 ml, 0.45 mol), and methylene chloride (600 ml) were placed in a 1-liter four-necked round flask, and the mixture was cooled on ice. Hexadecanoylchloride (60 g, 0.27 mol) was added dropwise over 3 hours to the flask while the contents of the flask were stirred under nitrogen. The mixture was stirred for 24 more hours at room temperature. The solid which precipitated was removed by filtration, and the solvent was removed under reduced pressure. Ethanol (600 ml) and an aqueous 4N NaOH solution (225 ml, 0.9 mol) were added to the residue and the mixture was stirred at 40° C. for 3 hours. The solvent was removed under reduced pressure. Methylene chloride was added and extraction was performed. After methylene chloride was removed from the organic phase under reduced pressure, the residue was purified by column chromatography (packed with Kieselgel 60 (product of Merck), eluent:chloroform/methanol=7:1 (v/v)) to obtain 6.0 g of 4,8-bis(1-oxohexadecyl)-1,11-di(dimethylamino)-6-hydroxy-4,8-diazaundecane. Yield: 9.1 wt %.

The thus-obtained compound (6.0 g, 0.0082 mol), methyl chloride (20 g, 0.36 mol), sodium carbonate (0.17 g, 0.0016 mol), isopropyl alcohol (100 ml), and water (20 ml) were placed into a 500-ml autoclave, and the temperature was elevated to 70° C. This temperature (70° C.) was maintained for 6 hours, and the flask was then allowed to cool to room temperature. The solvent was evaporated under reduced pressure. The residue was dissolved in chloroform (300 ml) and washed with water. Chloroform was distilled off under reduced pressure to give 6.5 g of 4,8-bis(1-oxohexadecyl)-1,11-di(trimethylammonium)-6-hydroxy-4,8-diazaundecane chloride. Yield: 95 wt %. High performance liquid chromatography (column: RP-18 (Merck), eluent:methanol/water=9:1 (v/v) (20 mM tetrabutylammonium bromide)) confirmed that this compound was not a mixture but a single product.

$^1$H-NMR(CD$_3$OD-CDCl$_3$):δ (ppm)
0.88 (6H, triplet, a)
1.27 (48H, singlet, b)
1.62 (4H, broad singlet, c)
1.95–2.25 (4H, complex multiplet, d)
2.25–2.7 (4H, complex multiplet, e)
3.17 (6H, singlet, f-1)
3.18 (6H, singlet, f-2)
3.22 (6H, singlet, f-3)

Example 5

2,14-Dimethyl-8-hydroxy-2,6,10,14-tetrazapentadecane 2HCl (30 g, 0.09 mol) synthesized in accordance with the method described in DE2616411, triethylamine (62 ml, 0.45 mol), and methylene chloride (600 ml) were placed in a 1-liter four-necked round flask, and the mixture was cooled on ice. Hexanoylchloride (36.3 g, 0.27 mol) was added dropwise over 3 hours to the flask while the contents of the flask were stirred under nitrogen. The mixture was stirred for 24 more hours at room temperature. The solid which precipitated was removed by filtration, and the solvent was removed under reduced pressure. Ethanol (600 ml) and an aqueous 4N NaOH solution (225 ml, 0.9 mol) were added to the residue and the mixture was stirred at 40° C. for 3 hours. The solvent was removed under reduced pressure. Methylene chloride was added and extraction was performed. After methylene chloride was removed from the organic phase under reduced pressure, the residue was purified by column chromatography (packed with Kieselgel 60 (product of Merck), eluent:chloroform/methanol=7:1 (v/v)) to obtain 20 g of 4,8-bis(1-oxohexyl)-1,11-di(dimethylamino)-6-hydroxy-4,8-diazaundecane. Yield: 50 wt %.

The thus-obtained compound (10 g, 0.023 mol), methyl chloride (4.6 g, 0.091 mol), sodium carbonate (0.5 g, 0.0046 mol), isopropyl alcohol (100 ml), and water (20 ml) were placed into a 500-ml autoclave, and the temperature was elevated to 70° C. This temperature (70° C.) was maintained for 6 hours, and the flask was then allowed to cool to room temperature. The solvent was evaporated under reduced pressure. The residue was dissolved in chloroform (300 ml) and insoluble salts were removed by filtration. Chloroform was removed under reduced pressure to give 12 g of 4,8-bis(1-oxohexyl)-1, 11-di(trimethylammonium)-6-hydroxy-4,8-diazaundecane chloride. Yield: 98 wt %. High performance liquid chromatography (column: RP-18 (Merck), eluent:methanol/water=9:1 (v/v) (20 mM tetrabutylammonium bromide)) confirmed that this compound was not a mixture but a single product.

$^1$H-NMR(CD$_3$OD-CDCl$_3$):δ (ppm)
0.88 (9H, triplet, a)
1.27 (8H, broad singlet, b)
1.62 (4H, broad singlet, c)
1.95–2.25 (4H, complex multiplet, d)
2.25–2.7 (4H, complex multiplet, e)
3.17 (6H, singlet, f-1)
3.18 (6H, singlet, f-2)
3.22 (6H, singlet, f-3)

3.25–3.75 (12H, complex multiplet, g)
4.06 (1H, broad singlet, h)

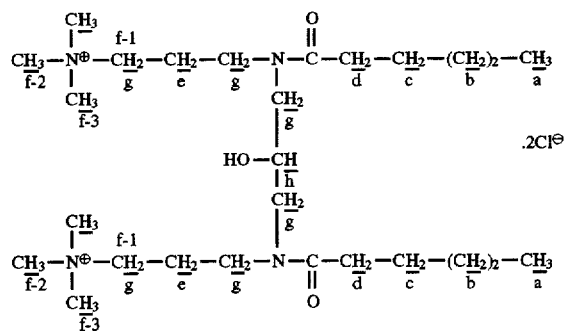

Example 6

Bis(2-hydroxy-8-methyl-4,8-diazanonyl)ether (10 g, 0.030 mol) synthesized using a known method, triethylamine (6.1 g, 0.060 mol), and methylene chloride (200 ml) were placed in a 500 ml four-necked round flask, and the mixture was cooled on ice. Dodecanoylchloride (13 g, 0.060 mol) was added dropwise over 1 hour to the flask while the contents of the flask were stirred under nitrogen. The mixture was stirred for 24 more hours at room temperature. The solid which precipitated was removed by filtration, after which water was added for washing. Methylene chloride was removed from the organic phase under reduced pressure. The residue was purified by column chromatography (packed with Kieselgel 60 (product of Merck), eluent:chloroform/methanol=7:1 (v/v)) to obtain 6.9 g of bis(4-(1-oxododecyl)-2-hydroxy-8-methyl-4,8-diazanonyl)ether. Yield: 33 wt %.

The thus-obtained compound (5 g, 0.0072 mol), methyl chloride (2.0 g, 0.040 mol), sodium carbonate (0.85 g, 0.008 mol), isopropyl alcohol (100 ml), and water (20 ml) were placed into a 500-ml autoclave, and the temperature was elevated to 70° C. This temperature (70° C.) was maintained for 6 hours, and the flask was then allowed to cool to room temperature. The solvent was evaporated under reduced pressure. The residue was dissolved in chloroform (300 ml) and washed with water. Chloroform was distilled off under reduced pressure to give 5.4 g of 4,12-bis(1-oxododecyl)-1,15-di(trimethylammonium)-4, 12-diaza-8-oxypentadecane dichloride. Yield: 98 wt %. High performance liquid chromatography (column: RP-18 (Merck), eluent:methanol/water=9:1 (v/v) (20 mM tetrabutylammonium bromide)) confirmed that this compound was not a mixture but a single product.

$^1$H-NMR(CD$_3$OD-CDCl$_3$):δ (ppm)
0.88 (6H, triplet, a)
1.27 (32H, singlet, b)
1.62 (4H, broad singlet, c)
1.95–2.25 (4H, complex multiplet, d)
2.25–2.7 (4H, complex multiplet, e)
3.17 (6H, singlet, f-1)
3.18 (6H, singlet, f-2)
3.22 (6H, singlet, f-3)

3.25–3.75 (16H, complex multiplet, g)
3.90 (2H, broad singlet, h)

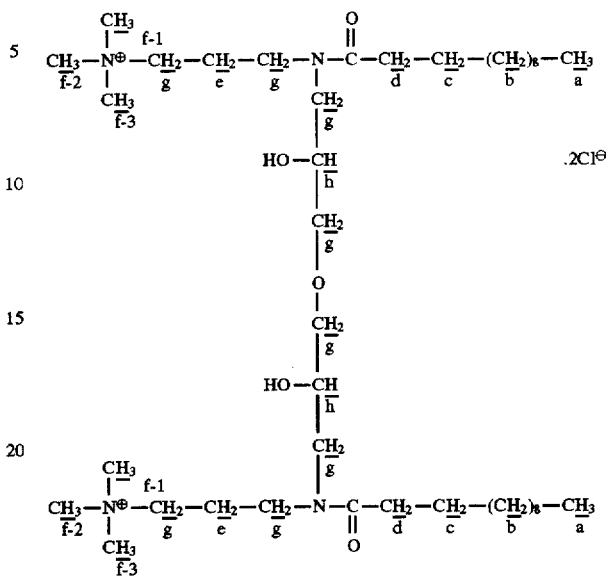

Example 7

Bis(2-hydroxy-8-methyl-4,8-diazanonyl)ether (10 g, 0.030 mol) synthesized using a known method, triethylamine (6.1 g, 0.060 mol), and methylene chloride (200 ml) were placed in a 500 ml four-necked round flask, and the mixture was cooled on ice. Hexadecanoylchloride (16.5 g, 0.060 mol) was added dropwise over 1 hour to the flask while the contents of the flask were stirred under nitrogen. The mixture was stirred for 24 more hours at room temperature. The solid which precipitated was removed by filtration, after which water was added for washing. Methylene chloride was removed from the organic phase under reduced pressure. The residue was purified by column chromatography (packed with Kieselgel 60 (product of Merck), eluent:chloroform/methanol=7:1 (v/v)) to obtain 4.9 g of bis(4-(1-oxohexadecyl)-2-hydroxy-8-methyl-4,8-diazanonyl)ether. Yield: 20 wt %.

The thus-obtained compound (4 g, 0.0049 mol), methyl chloride (2.0 g, 0.040 mol), sodium carbonate (0.85 g, 0.008 mol), isopropyl alcohol (100 ml), and water (20 ml) were placed into a 500-ml autoclave, and the temperature was elevated to 70° C. This temperature (70° C.) was maintained for 6 hours, and the flask was then allowed to cool to room temperature. The solvent was evaporated under reduced pressure. The residue was dissolved in chloroform (300 ml) and washed with water. Chloroform was removed under reduced pressure to give 4.1 g of 4,12-bis(1-oxohexadecyl)-1,15-di(trimethylammonium-4, 12-diaza-8-oxypentadecane dichloride. Yield: 96 wt %. High performance liquid chromatography (column: RP-18 (Merck), eluent:methanol/water=9:1 (v/v) (20 mM tetrabutylammonium bromide)) confirmed that this compound was not a mixture but a single product.

$^1$H-NMR(CD$_3$OD-CDCl$_3$):δ (ppm)
0.88 (6H, triplet, a)
1.27 (48H, singlet, b)
1.62 (4H, broad singlet, c)
1.95–2.25 (4H, complex multiplet, d)
2.25–2.70 (4H, complex multiplet, e)
3.17 (6H, singlet, f-1)
3.18 (6H, singlet, f-2)
3.22 (6H, singlet, f-3)

3.25–3.75 (16H, complex multiplet, g)
3.90 (2H, broad singlet, h)

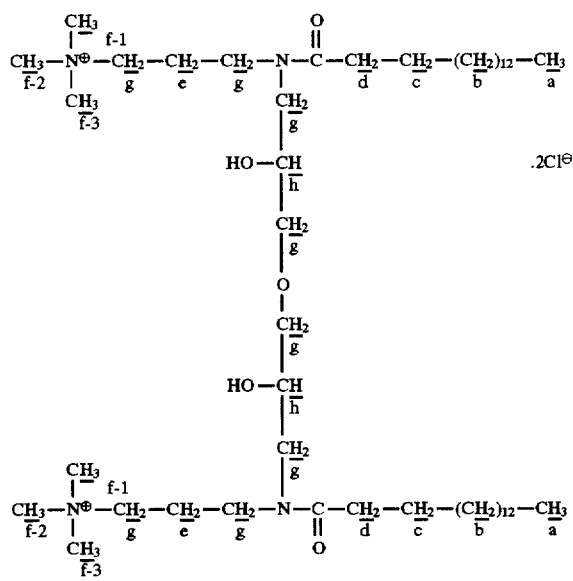

Example 8

Into a four-necked flask containing ethylenediamine (3 g, 0.05 mol) and water (50 g), propanesultone (12.3 g, 0.1 mol) was added dropwise over 30 minutes. The contents were mixed for 2 hours, after which ethanol was added thereto. The mixture was subjected to filtration and then was washed with ethanol to obtain 13.5 g of N,N'-bis(3-sulfopropyl) ethylenediamine (separation yield: 88 wt %).

Subsequently, N,N'-bis(3-sulfopropyl)ethylenediamine (5 g, 0.016 mol), water (30 g), and acetone (13 g) were placed in a four-necked flask. The pH of the contents was adjusted to 8.5 with an aqueous 4N NaOH solution. The flask was cooled to 10° C., and caprylic chloride (5.3 g, 0.033 mol) was added dropwise. Since pH falls as the reaction proceeds, an aqueous 4N NaOH solution was added if necessary to maintain the pH between 9 and 10. When the caprylic chloride had been completely added, the mixture was stirred for 1 hour. Water was removed using an evaporator while the mixture underwent azeotropic distillation with ethanol. Thereafter, water (250 g) was added and the mixture was filtered to remove insoluble matter. The residue was desalted by electrodialysis and then freeze-dried to obtain 3.0 g of disodium 4,7-dioctanoyl-4,7-diazadecane-1, 10-disulfonate (separation yield: 31 wt %). Mass analysis (FAB ionization method) m/z: 601(M+H$^+$), m=$C_{24}H_{46}S_2O_8N_2Na_2$.

$^1$H-NMR(CDCl$_3$, δ ppm):
0.83(t, 6H, a), 1.27(broad, 16H, b), 1.58(m, 4H, c), 2.00(m, 4H, d), 2.34(t, 4H, e), 2.89(t, 4H, f), 3.40–3.62(m, 8H, g)

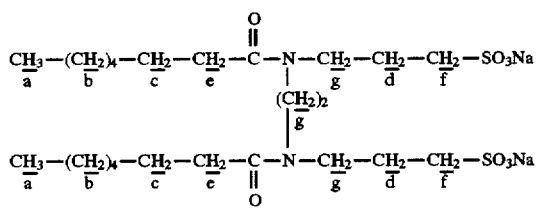

Example 9

Into a four-necked flask containing ethylenediamine (3 g, 0.05 mol) and water (50 g), an aqueous sodium chloroacetate solution (11.7 g, 0.1 mol) was added dropwise over 30 minutes. The contents were mixed at 60° C. for 2 hours, and then washed with ethanol to give 8.8 g of N,N'-bis (carboxymethyl) ethylenediamine (separation yield: 88 wt %).

Subsequently, N,N'-bis(carboxymethyl)ethylenediamine (5 g, 0.028 mol), water (30 g), and acetone (13 g) were placed in a four-necked flask. The pH of the contents was adjusted to 8.5 with an aqueous 4N NaOH solution. The flask was cooled to 10° C., and caprylic chloride (9.3 g, 0.057 mol) was added dropwise. Since pH falls as the reaction proceeds, an aqueous 4N NaOH solution was added if necessary to maintain the pH between 9 and 10. When the caprylic chloride had been completely added, the mixture was stirred for 1 hour. Water was removed using an evaporator while the mixture underwent azeotropic distillation with ethanol. Thereafter, water (250 g) was added and the mixture was filtered to remove insoluble matter. The residue was desalted by electrodialysis and then freeze-dried to obtain 4.6 g of a disodium salt of 3,6-dioctanoyl-3,6-diazaoctane diacid (separation yield: 35 wt %). Mass analysis (FAB ionization method) m/z: 473(M+H$^+$), m=$C_{22}H_{38}O_6N_2Na_2$.

$^1$H-NMR(CDCl$_3$, δ ppm):
0.85(t, 6H, a), 1.29(broad, 16H, b), 1.61(m, 4H, c), 2.34(t, 4H, d), 3.40–3.62(m, 4H, e), 4.11(s, 4H, f)

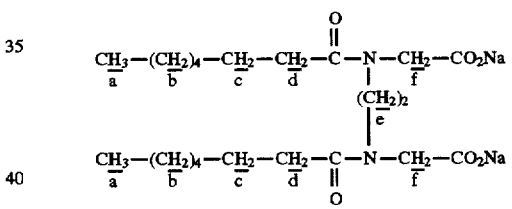

Example 10

N,N'-bis(2-Hydroxyethyl)ethylenediamine (5 g, 0.034 mol), water (30 g), and acetone (13 g) were placed in a four-necked flask. The pH of the contents was adjusted to 8.5 with an aqueous 4N NaOH solution. The flask was cooled to 10° C., and caprylic chloride (11.6 g, 0.071 mol) was added dropwise. Since pH falls as the reaction proceeds, an aqueous 4N NaOH solution was added if necessary to maintain the pH between 9 and 10. When the caprylic chloride had been completely added, the mixture was stirred for 1 hour. Thereafter, the mixture was stirred for 3 hours at room temperature. The solvent was distilled off and the residue was dissolved in dichloromethane. Chlorosulfonic acid was added dropwise to the solution, followed by stirring for 1 hour. The mixture was then stirred for 3 hours at room temperature. Thereafter, water (250 g) was added and the pH was adjusted to 7. The mixture was filtered to remove insoluble matter. The residue was desalted by electrodialysis and then freeze-dried, obtaining 6.0 g of a disodium 3,6-dioctanoyl-1,8-disulfonate (separation yield: 35 wt %). Mass analysis (FAB ionization method) m/z: 605(M+H$^+$), m=$C_{22}H_{42}S_2O_{10}N_2Na_2$.

$^1$H-NMR(CDCl$_3$, δ ppm):
0.88(t, 6H, a), 1.29(broad, 16H, b), 1.66(m, 4H, c), 2.30(t, 4H, d), 3.41–3.66(m, 8H, e), 4.44(broad, 4H, f)

$$\underset{a}{CH_3}-\underset{b}{(CH_2)_4}-\underset{c}{CH_2}-\underset{d}{CH_2}-\overset{O}{\underset{\|}{C}}-N-\underset{e}{CH_2}-\underset{f}{CH_2}-OSO_3Na$$
$$\qquad\qquad\qquad\qquad\qquad\underset{e}{|}$$
$$\qquad\qquad\qquad\qquad\quad(CH_2)_2$$
$$\underset{a}{CH_3}-\underset{b}{(CH_2)_4}-\underset{c}{CH_2}-\underset{d}{CH_2}-\underset{\underset{O}{\|}}{C}-N-\underset{e}{CH_2}-\underset{f}{CH_2}-OSO_3Na$$

Formulation Example 1

Using the compound of the present invention prepared in Example 1, a shampoo having the following composition was prepared.
Composition

| Compound prepared in Example 1 | 15.0 (wt %) |
|---|---|
| Lauroyl diethanolamide | 3.0 |
| Lauryl dimethylamine oxide | 0.5 |
| Hydroxyethylcellulose (DICEL) | 0.1 |
| Sodium benzoate | 0.3 |
| Colorant | suitable amount |
| Perfume | suitable amount |
| Citric acid | suitable amount |
| Water | balance |
| Total | 100.0 |

Formulation Example 2

The procedure of Formulation Example 1 was repeated using each of the compounds prepared in Examples 2 through 10 in place of the compound prepared in Example 1 to prepare shampoo compositions.

All the shampoo compositions prepared in Formulation Examples 1 and 2 exhibited excellent latherability and detergency. They also provided a pleasant sensation during shampooing and rinsing.

Formulation Example 3

Using the compound of the present invention prepared in Example 1, a body shampoo having the following composition was prepared.
Composition

| Compound prepared in Example 1 | 17.0 (wt%) |
|---|---|
| Polyoxyethylene (E03) laurylglucoside | 5.0 |
| Lauryl dimethylamine oxide | 3.0 |
| Glycerol | 4.0 |
| Sucrose fatty acid ester | 1.0 |
| Methylparaben | 0.3 |
| Colorant | suitable amount |
| Perfume | suitable amount |
| Citric acid | suitable amount |
| Water | balance |
| Total | 100.0 |

Formulation Example 4

The procedure of Formulation Example 3 was repeated using each of the compounds prepared in Examples 2 through 10 in place of the compound prepared in Example 1 to prepare body shampoo compositions.

All the body shampoo compositions prepared in Formulation Examples 3 and 4 exhibited excellent latherability and detergency. They also provided a pleasant moistened sensation after use.

The novel amide compounds (1) of the present invention are mild to the skin and hair, provide a pleasant sensation to the skin and hair, and have excellent latherability and emulsion stability. Thus, they are useful as components of detergents, cosmetic compositions, etc. as well as emulsifiers, conditioners, etc.

Obviously, numerous modifications and variations of the present invention are possible in light of the above teachings. It is therefore to be understood that, within the scope of the appended claims, the invention may be practiced otherwise than as specifically described herein.

This application is based on Japanese Patent Application Nos. 7-110335 filed on May 9, 1995, 7-118219 filed on May 17, 1995, 7-137735 filed on Jun. 5, 1995 and 7-137736 filed on Jun. 5, 1995, which are incorporated herein by reference in their entireties.

What is claimed as new and is desired to be secured by Letters Patent of the United States is:

1. An amide having the formula (I):

$$R^1-\overset{O}{\underset{\|}{C}}-\underset{\underset{Y^1}{\underset{|}{A^1}}}{N}-B-\underset{\underset{Y^2}{\underset{|}{A^2}}}{N}-\overset{O}{\underset{\|}{C}}-R^2 \qquad (1)$$

wherein:
  R$^1$ and R$^2$ are identical to or different from each other, and are each independently unsubstituted or hydroxyl-substituted linear or branched C7–C15 alkyl;
  B is unsubstituted or hydroxyl-substituted linear or branched C2–C10 alkylene or B is a group of the formula:

—CH$_2$CH(OH)CH$_2$O(CH$_2$CH$_2$O)$_p$CH$_2$CH(OH)(CH$_2$— wherein p is an integer from 0 to 2 inclusive;
  A$^1$ and A$^2$ are identical to or different from each other, and each is independently unsubstituted, hydroxyl-substituted or carboxyl-substituted linear or branched C1–C6 alkylene; and
  Y$^1$ and Y$^2$ are identical to or different from each other, and each is independently —COOH, —SO$_3$H, —SO$_4$H, —NR$_3$R$_4$, or $$-\underset{\underset{R^5}{|}}{\overset{\overset{R^3}{|}}{N^\oplus}}-R^4 X^{\ominus},$$

wherein R$^3$, R$^4$ and R$^5$ are identical to or different from one another and each independently is unsubstituted or hydroxyl-substituted linear or branched C1–C4 alkyl or alkenyl and X$^1$ is halogen; or a salt thereof.

2. The amide of claim 1, wherein
  R$^1$ and R$^2$ are identical to or different from each other, and each is linear or branched C17–C15 alkyl.

3. The amide of claim 1, wherein
  R$^1$ and R$^2$ are identical to or different from each other, each is linear or branched C7–C15 alkyl,
  B is unsubstituted or hydroxyl-substituted linear C2–C10 alkylene;

$A^1$ and $A^2$ are identical or different from each other, each is linear or branched C1–C6 alkylene, $Y^1$ and $Y^2$ are identical to or different from each other, each is

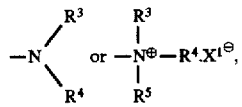

wherein $R^3$, $R^4$, and $R^5$ are identical to or different from one another and each independently is unsubstituted or hydroxyl-substituted linear or branched C1–C4 alkyl or alkenyl and $X^1$ is halogen.

4. The amide of claim 1, wherein B is unsubstituted or hydroxyl-substituted linear C2–C6 alkylene.

5. The amide of claim 1, wherein B is —CH$_2$CH(OH)CH$_2$O(CH$_2$CH$_2$O)PCH$_2$CH(OH)CH$_2$— wherein p is an integer from 0–2.

6. The amide of claim 6, wherein p=0.

7. The amide of claim 1, wherein $X^1$ is bromine or chlorine.

8. The amide of claim 3, wherein $R^3=R^4=R^5=CH_3$.

9. The amide of claim 1, wherein $Y^1$ or $Y^2$ is —COOH.

10. The amide of claim 1, wherein $Y^1$ or $Y^2$ is —SO$_3$H or —SO$_4$H.

11. The amide of claim 1, wherein each of $R^1$ and $R^2$ are independently selected from the group consisting of heptyl, octyl, nonyl, decyl, undecyl, dodecyl, tridecyl, tetradecyl, pentadecyl, methyl hexyl, ethyl hexyl, methyl heptyl, ethyl heptyl, methyl nonyl and methyl undecyl.

12. The amide of claim 11, wherein each of $R^1$ and $R^2$ are independently selected from the group consisting of undecyl and pentadecyl.

* * * * *